United States Patent [19]

Henkin

[11] 4,066,405
[45] Jan. 3, 1978

[54] METHOD FOR TOTAL PROTEIN FRACTIONATION AND ANALYSIS OF HUMAN SALIVA

[75] Inventor: Robert I. Henkin, Bethesda, Md.

[73] Assignee: The United States of America as represented by the Department of Health, Education and Welfare, Washington, D.C.

[21] Appl. No.: 729,157

[22] Filed: Oct. 4, 1976

Related U.S. Application Data

[63] Continuation of Ser. No. 547,464, Feb. 6, 1975, abandoned.

[51] Int. Cl.² .................... G01N 33/16; G01N 21/00; G01N 21/52; G01N 31/08
[52] U.S. Cl. ........................... 23/230 B; 260/112 R; 260/113
[58] Field of Search ............... 23/230 B; 424/145; 260/113

[56] References Cited

U.S. PATENT DOCUMENTS

3,763,136  10/1973  Huber .................................. 260/113

OTHER PUBLICATIONS

"Advances in Protein Chem.," C. B. Anfinsen et al., eds., Academic Press, vol. 17, 209-226, 303-315, 378-390 (1962).
Croft, Biochem. J., vol. 130, 303-305 (1972).
Chemical Abstracts I, 77: 84718r (1972).
Chemical Abstracts II, 79: 50026q (1973).
Chemical Abstracts III, 72: 74756j, (1970).
Chemical Abstracts IV, 83: 93311d (1975).

*Primary Examiner*—Sidney Marantz

[57] ABSTRACT

A method for the total protein fractionation of saliva and for isolating a novel zinc protein found to be a component thereof is disclosed. Saliva was fractionated using three protein parameters and zinc concentration by a molecular sieving process. The zinc protein was isolated and purified from the saliva of subjects with normal taste acuity by gel filtration and ion exchange chromatography maximizing these parameters. The zinc protein has a molecular weight of 37,000 and does not appear to have subunits. It is composed of 8% histidine residues and has two moles of zinc per mole of protein. A decreased concentration of the protein in saliva has been associated with abnormal taste acuity.

37 Claims, 4 Drawing Figures

METHOD FOR TOTAL PROTEIN FRACTIONATION AND ANALYSIS OF HUMAN SALIVA

This is a continuation of application Ser. No. 547,464, filed Feb. 6, 1975, now abandoned.

This invention relates to the discovery of the presence of a zinc protein in human saliva. More importantly, this invention relates to a laboratory procedure for the total protein fractionation of saliva to isolate constituents thereof for diagnostic evaluation, which procedure was used to isolate this protein. The zinc protein found to be a normal constituent of parotid saliva demonstrates chemical and molecular characteristics different from any zinc containing protein previously known. The zinc protein, named gustin, has been demonstrated to be essential to the taste process.

In my prior U.S. Pat. Nos. 3,743,088 and 3,852,432 an apparatus for testing taste acuity was disclosed, and a method for the treatment of abnormal taste acuity, hypogeusia, by ingestion of zinc containing salts was described.

While saliva has been shown to play an important role in taste, the contributing factors therein were previously not known. Patients suffering with xerostomia (decreased or absent saliva) exhibit hypogeusia (decreased taste acuity) which can be correlated with pathological changes in taste bud anatomy. See for example Henkin et al. *Ann. Int. Med.*, 76: 375–383 (1972). Decreased taste acuity has also been observed in rats in which the salivary glands have been extripated. In the case of patients with xerostomia the oral administration of water or saline, with or without other electrolytes, failed to restore taste function. However, if patients suffering with xerostomia are treated with agents which restore salivary function, normal taste acuity has been recovered.

As pointed out in my above patents, patients have been observed to contract hypogeusia while maintaining normal salivary flow rates. In such patients a pathological change in the taste buds is also commonly observed, and this change is similar to those changes observed in patients with xerostomia.

Zinc has been shown to play an important role in taste perception. Patients with hypogeusia exhibit significantly lower than normal concentrations of zinc in serium and parotid saliva. See for example Mueller and Henkin *Fed. Proc.* 33: 700 (1974). Oral administration of zinc to some patients with hypogeusia has resulted in normalization of the serum and parotid zinc levels, taste perception, and taste bud anatomy. Although the foregoing suggests a role for zinc in taste, its function was unclear prior to the instant invention. This lack of resolution stemmed from the fact that prior to this invention no practical procedure for the total protein fractionation of saliva had been developed for use as a diagnostic tool.

From the physiological, anatomical and clinical observations of taste perception and from the knowledge that zinc is normally found associated with protein in biological fluids it was first hypothesized, and as will be subsequently explained, proven, that a zinc protein is a normal constituent of parotid saliva, and that its function is related to taste whereby decreased taste acuity is associated with abnormally low concentrations of the protein in saliva. In order to prove the hypothesis it was necessary to devise a process for total protein fractionation of saliva.

Accordingly it has been discovered that saliva may be fractionated by gel filtration and also evaluated with ion exchange chromotography to isolate the protein components for diagnosis of abnormalities. The process of this invention essentially fractionates by maximizing three distinctive protein properties, against zinc concentration. The three properties are exhibited by spectroscopic methods which evaluate absorption of 215 nm and 280 nm and fluorescence at 340 nm. Absorption at 280 nm is determined principally by the amount of tyrosine and tryptophan in the protein. Intensity of fluorescence at 340 nm is dependent upon the tryptophan quantum yield of the protein, and absorption at 215 nm is determined principally by the peptide chromophore although minor differences will arise if aromatic chromophores are present in unusual amounts. In the process of this invention the difference in absorption between 215 nm and 225 nm, called $\Delta$ 215, was used in order to eliminate any absorption due to turbidity.

By using the above parameters protein in saliva may be totally fractionated by molecular sieving in for example a Sephadex G 150 column (obtained from Pharmacia, Upsala, Sweden). The zinc protein may then be isolated by further chromatography combining the steps of molecular sieving and ion exchange in for example a DEAE-A50 column (obtained from Pharmacia, Upsala, Sweden) and finally by ion exchange in carboxymethylcellulose (CM 52, preswollen) column obtained from W. & R. Balston, Ltd., London, England. In each of the above steps separation is achieved based on molecular sieving change characteristics and slight differences in aromaticity of the components. The process of this invention then resulted in isolation of the taste related zinc protein, gustin.

This was indicated by (a) the presence of one band by gel electrophoresis in phosphate buffer, with and without sodium dodecyl sulfate (SDS); (b) a symmetrical peak on the carboxymethylcellulose (CMC) column in which the ratio of zinc to any of the three protein parameters and the ratio of each of the protein parameters to the others was constant across the peak, and (c) the linearity of the plot of the ln c versus $R^2$ in sedimentation equilibrium experiments.

The molecular sieving action of the Sephadex G 150 column has been found to result in total protein fractionation permitting the elimination of the major portion of the contaminating 280 nm adsorbing material while subsequent ion exhange in the DEAE-A50 Sephadex column results in eliminating the major portion of the contaminating $\Delta$ 215 material. The zinc protein then was isolated by maximizing the three protein parameters and zinc concentration in each purification step. As will be subsequently pointed out, the results indicate that a 200 fold purification of the zinc protein was accomplished by the aforementioned three chromotographic procedures.

The protein isolated from normal parotid saliva, was found present at much lower levels in the saliva of patients with hypogeusia. In addition, by monitoring saliva of these patients it was established that zinc, intraveneously injected, is rapidly incorporated into the zinc protein in vivo. This is merely one example of utility for the instant process for total protein fractionation of saliva as a diagnostic tool.

Accordingly it is an object of this invention to provide a laboratory procedure for the total protein fractionation of saliva.

It is another object to provide a process for the total protein fractionation of saliva utilizing protein parameters of absorption at 215 nm and 280 nm and fluorescence at 340 nm against zinc concentration in molecular sieving chromotography.

It is another object of this invention to provide a laboratory procedure for isolating and evaluating a zinc protein found to be a constituent of parotid saliva.

It is another object to provide a method for evaluating human saliva to determine the presence and level of concentration of a zinc protein found to be related to taste acuity.

It is still another object to provide a method for fractionating human saliva by gel filtration and ion exchange chromatography to isolate a zinc containing protein having a molecular weight of 37,000, composed of 8% histidine residues with two moles zinc per mole of protein.

It is yet another object to provide a diagnostic method for evaluating taste acuity by fractionating saliva to isolate and evaluate a taste related zinc-containing protein therein.

These and other objects will become readily apparent with reference to the drawings and following description wherein.

The following is a description of the laboratory procedure of this invention.

In order to collect and prepare parotid saliva samples for analysis according to the process of this invention saliva was collected in plastic Lashley cups placed over Stenson's ducts and salivary flow was stimulated by the timed oral administration of lemon juice. By this technique whole parotid saliva, uncontaminated with saliva from any other source, was collected. The saliva was then lyophilized in acid washed, glass flasks. When needed, the dry product was transferred to plastic centerfuge tubes, dissolved in 5 mls zinc free distilled water and allowed to stand in ice for 1 to 3 hours.

The reconstituted saliva was centrifuged at 20000 × g for 30 minutes at 0° to remove flocculent material and insoluble protein. This precipitate was tested, initially, but zinc could not be identified therein. The clear supernatant fluid was used in all subsequent procedures.

The water, reagents, and glassware used in the process of this invention were tested and demonstrated to be free of zinc as measured by atomic atmospheric spectrophotometry. See Meret and Henkin, *Clin. Chem.* 17: 369–373 (1971). The glassware was normally soaked for 24–48 hours in 6 N HCl and then rinsed thoroughly with zinc free water prior to use. Dialysis tubing was soaked in 0.01 M ethylenediamine tetraacidic acid (EDTA) for 24–72 hours, rinsed, soaked and stored in zinc free water until ready for use. Plastic vessels, polyethylene tubing and connectors, and plastic coated or covered stoppers were used whenever possible since they are not contaminated with zinc as is glass.

Chromotography

Total protein fractionation is, as noted above, achieved by separating the saliva into aliquots on the basis of molecular weight, and monitoring three essential protein parameters against zinc concentration in the aliquots. The following is a preferred procedure therefor.

The lyophilized parotid saliva is dissolved in 0.10 M phosphate buffer, pH 6.8 (about 800 milligrams protein), and is applied on a Sephadex G-150 column (2.5 × 90 cm) which is equilibrated with 0.10 M phosphate buffer, pH 6.8.

Figure 1:
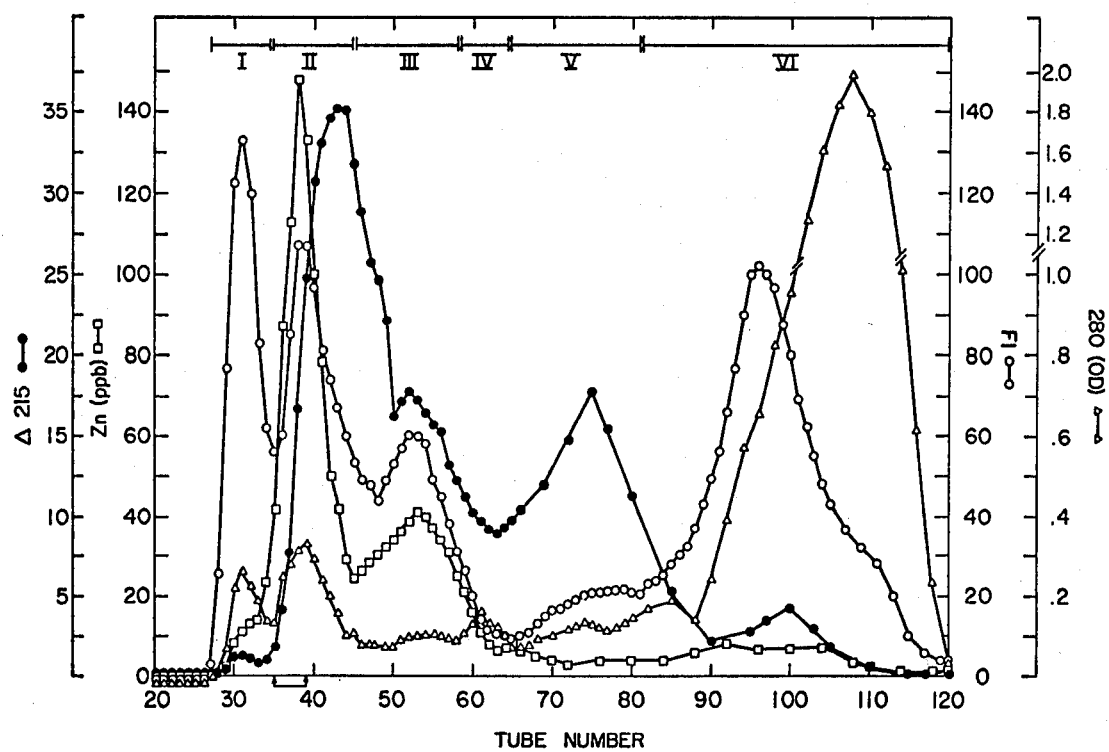
FIG. 1 is a graph representative of the Sephadex G 150 chromatography of whole parotid saliva wherein the column was eluted with 0.01 M phosphate buffer, pH 6.8, as compared to zinc concentration in parts per billion (ppb)

FIG. 1 is an example of a typical result with gel filtration. The parotid saliva analyzed in FIG. 1 came from a woman from whom collections were obtained on 24 separate occasions. Saliva from about ⅔ of these collections were eluted on the same Sephadex G-150 column and the major features of the patterns shown in FIG. 1 were reproduced. The basic features of this pattern were observed in the saliva obtained from other subjects with normal taste acuity although some differences were found. In other subjects with normal taste acuity the zinc was actually distributed over a wider range, frequently extending into Fraction III.

The elution profiles as described above were obtained by using three methods of protein analysis. These three methods are quite distinct since different protein properties are measured by each technique. The $\Delta 215$ and 280 nm absorbances were measured in this fractionation as well as subsequent purifications in a Gilford spectrophotometer, obtainable from Gilford Instrument Laboratories, Inc., Oberlin, Ohio.

Emission intensities were measured with a Perkin-Elmer Co., Norwalk, Connecticut, attached to a chart drive read-out system. and emission at 340 nm) obtainable from Perkin Elmer Co., Norwalk, Conn.

A dilute aqueous solution of acetyltryptophanamide was used to yield the standard fluorescent signal.

zinc was measured with an Instrumentation Laboratory Model 355 flameless sampler attached to an Instrumentation Laboratory Model 153 atomic absorption spectrophotometer. This apparatus is obtainable from Instrument Laboratories, Inc., Lexington, Mass. The method for evaluating zinc is also described in *Mueller and Henkin, Fed. Proc.* 33: 700 (1974). Zinc concentration in all column elutates was based upon comparison with a standard zinc curve.

The $\Delta 215$ aborption profile was divided into six major fractions, which are labelled I–VI in FIG. 1. Fraction I appeared in the solvent front and though highly fluorescent showed very little $\Delta 215$ absorption. Fraction II was divided into two parts (A, Tubes 35–39; B, Tubes 40–45). Since the protein in the first part (IIA) contained a much higher $Zn/\Delta 215$ ratio than in the second part (IIB), Fraction IIA was lyophilized for subsequent purification. Fraction IIA corresponds to a molecular weight of about 60,000 to 80,000.

In order to isolate the zinc protein lyophilized Fraction IIA was dissolved in 5 mls of zinc free water and dialized overnight against 0.01 M phosphate buffer at pH 6.8. The dialized solution (about 130 milligrams of protein) was then placed on a DEAE-A50 equilibriated with the same buffer. This column achieves further purification by a combination of molecular sieving and ion exchange.

Figure 2:
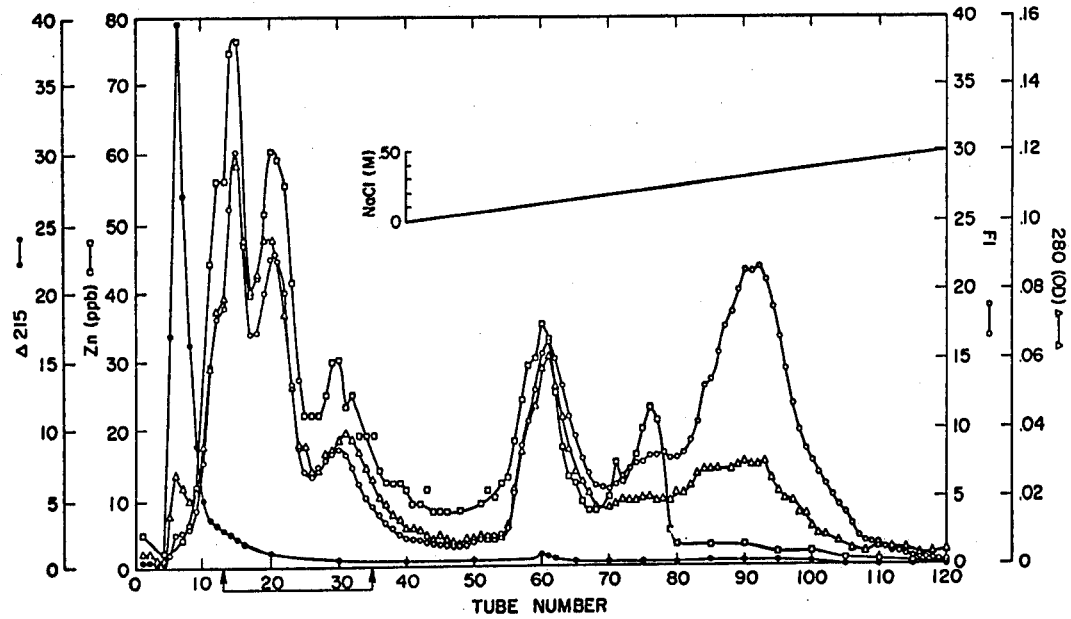
FIG. 2 is a graph of the DEAE A-50 Sephadex chromatography of the contents of tubes 35–39 from the Sephadex G 150 chromatography of FIG. 1. The column was eluted initially (tubes 1–41) with a 0.01 m phosphate buffer pH 6.8, and then with a continuous NaCl gradient (0.0 – 0.50 M) in the same buffer.

With attention to FIG. 2, tubes 1–40 were obtained by elution by the equilibriated buffer; whereas tubes 41–120 resulted from the linear gradient of NaCl (0–0.5 M). The major $\Delta 215$ absorption peak is herein separated from the zinc, fluorescence, and 280 nm absorption peaks and occurs before the NaCl gradient was started.

Three zinc peaks (two major and one minor) were resolved. These peaks resemble each other rather closely in that the Zn/280 nm/fluorescent ratio in each peak is similar. Elution with the NaCl gradient resolved two additional zinc peaks representing approximately 30% of the zinc on the column; however, the zinc/protein ratios of these peaks were lower than those obtained with the buffer alone and they were not used in subsequent analyses.

Figure 3:
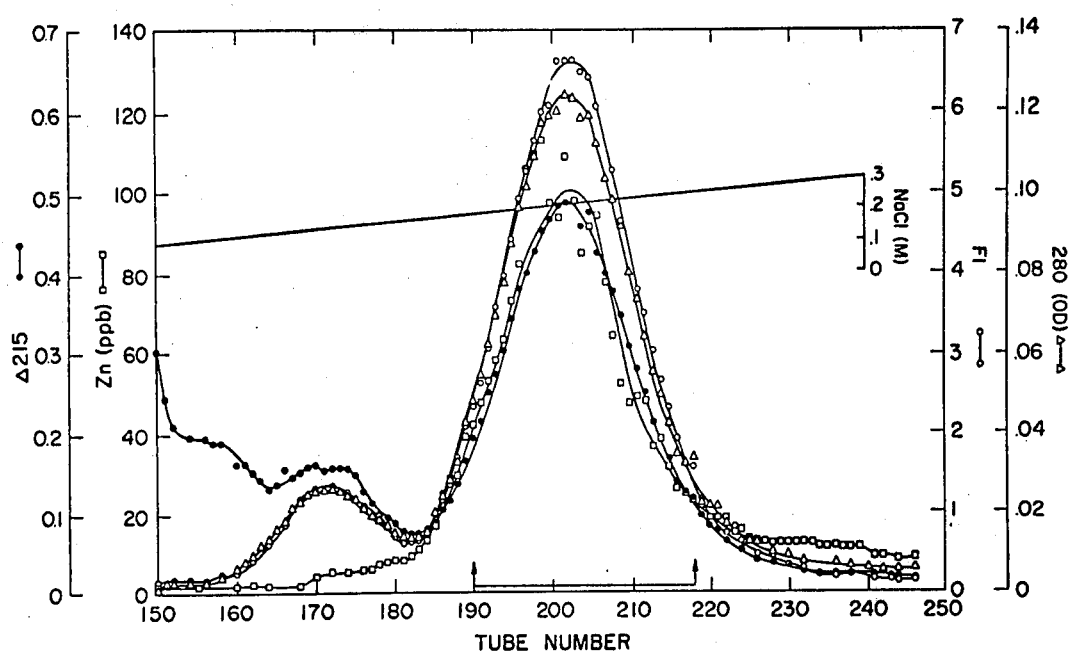
FIG. 3 is a graph of the carboxymethylcellulose chromatography of the contents of tubes 14–34 from the DEAE A-50 chromatography of FIG. 2. The column was eluded initially, tubes 1–86, with a 0.005 molar M phosphate buffer, pH 5.9, and then with a continuous NaCl gradient (0.0 – 0.3 M) in the same buffer.

With attention to FIG. 3, the contents of tubes 14–34 (shown by the bracket) which maximized the zinc protein parameters were pooled and lyophilized for further purification by ion exchange. The product was then dissolved in water and dialized for 24 hours against 0.005 M phosphate buffer, pH 5.9.

The dialized solution of tubes 14–34 (about 10 mg protein) was then subjected to a final purification on the CMC column (1.5 × 12 cm) and equilibriated with 0.005 M phosphate buffer, pH 5.9. With attention to FIG. 3, the initial tubes, 1–86, were obtained by elution with the buffer alone whereas tubes 87–240 resulted from a linear gradient of NaCl (0 – 0.30 M) in 0.005 M phosphate buffer, pH 5.9.

Two major protein peaks showing $\Delta 215$ absorption without significant 280 nm absorption, fluorescence, or zinc were resolved in tubes 1–86. The zinc was concentrated largely in the single peak centered at tube 202. The ratio of zinc to protein in this peak was constant between tubes 190 and 218 and independent of the parameter used to evaluate protein concentration, i.e. $\Delta 215$, absorption at 280 nm, or fluorescence.

In summary, then as shown in FIG. 1 the molecular sieve of gel filtration with Sephadex G-150, divided into six fractions, produced marked protein characteristics in the three parameters chosen, $\Delta 215$, the difference in absorption between 215 nm and 225 nm; 280 (OD) representing the absorption at 280 nm; and fluorescence (fl) representing the observed fluorescence at 340 nm with activation at 280 nm. When these protein characteristics are plotted with zinc concentration a total protein fractionation is presented for analysis.

The contents of the tubes maximizing these parameters, the zinc to protein ratios, could then be isolated for subsequent purification. In the instance of FIG. 1, the contents of tubes 35–39, shown thereon by a bracket on the abscissa were chosen for subsequent chromatography with DEAE-A=Sephadex to isolate the taste related protein.

FIG. 2 represents a second chromatographic analysis performed upon the contents of tubes 35–39 from the Sephadex G-150 column, which chromatographic analysis was performed upon the DEAE-A=Sephadex column. As shown by FIG. 2, the contents of tubes 14–34 maximized the zinc and protein parameters, and accordingly the contents of these tubes were selected for the third, successive, chromatographic analysis on the CMC column.

Finally, as shown in FIG. 3, when the contents of tubes 14–34 from the DEAE-A50 Sephadex column were analyzed on the CMC column a peak was produced wherein the ratio of zinc to protein was constant indicating the isolation of the zinc protein material.

Molecular Characterization of Gustin

In order to further evaluate the isolated zinc protein, electrophoresis of the purified zinc protein was carried out a pH 7.2 in 0.05 M phosphate buffer. Polyacrylamide gel electrphoresis was performed in continuous buffer systems with gel concentrations of 4% T, 4% C, and 7% T, 4% C based upon the nomenclature of Hjerten described in Arch. Biochm. Biophys. Suppl. 1, 147–151 (1962). Protein was stained with Coomassie brilliant blue R 250. See Webber and Osborne J. Biol. Chem. 244: 4406–4412 (1969). Electrophoresis at pH 7.2 in 0.1% SDS, 0.1 M sodium phosphate showed one major band and one faint, more slowly migrating band. The molecular weights of the major and minor components in the SDS gel, determined by comparison with appropriate standards, were 44,000 and 84,000 respectively.

After reduction with 2-mercaptoethanol electrophoresis in SDS showed no significant change in the migration of the major band although some diffuse staining was evident on either side of the major band.

The presence of one predominant band at pH 7.2 in either aqueous of SDS solutions, and the pattern of the minor bands observed at pH 8.9 suggest those minor bands are polymers of the native protein as observed frequently with serum albumen.

Figure 4:
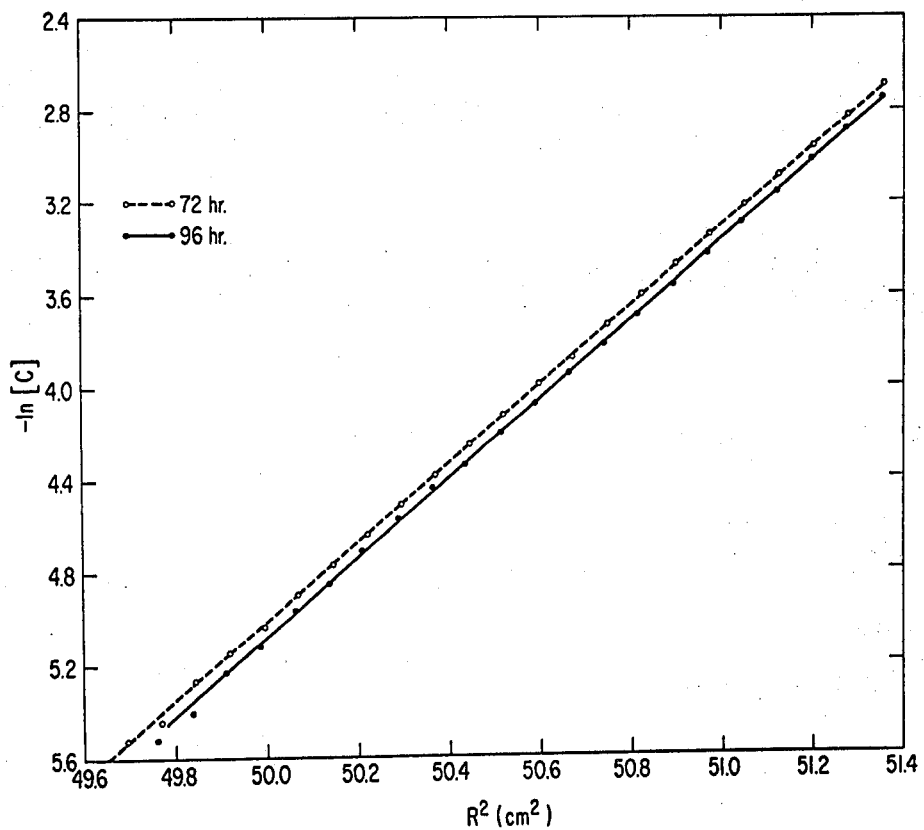
FIG. 4 is a graphical representation of sedimentation equilibrium of the parotid zinc protein in 0.1 M NaCl, 0.01 M phosphate buffer, pH 6.8. The square of that radial distance ($R^2$) is plotted against the negative logarithm of the protein concentration ($-lnC$) in grams per hundred milliliters.

With reference to FIG. 4, the molecular weight of the purified zinc protein was measured by sedimentation equilibrium in 0.10 M phosphate buffer, pH 6.8. No difference in molecular weight was found between 72 and 96 hours of concentration at 28,000 r.p.m. at 25° C. A linear dependence of ln c versus $R^2$ was observed, as shown in FIG. 4.

From the slope of the line a molecular weight of 37,000 was calculated by the Svedberg equation when a value of 0.723 was used for the partial specific volume. This value was computed from the amino acid composition of the purified protein and from the partial specific volume of the individual amino acids.

The molecular weight was obtained by equilibrium sedimentation in a Spinco Model E ultra-centrifuge with scanner optics, obtained from Beckman Instruments, Fullerton, Cal.

The method of meniscus depletion was used with a 4mm column height. Solutions were thoroughly dialyzed against either 0.1 M NaCl or 6.0 M guanidinium hydrochloride prior to centrifugation.

Neutral sugar content of the purified protein was determined by the phenol sulphuric acid method with galactose as a standard. See Ashwell Methods of Enzymology (Colowick and Kaplan Eds.) 8: 93–95 (1966).

As noted above the zinc was measured with an Instrumentation Laboratory Model 355 flameless sampler attached to an Instrumentation Laboratory Model 153 atomic absorption spectrophotometer, with zinc concentration evaluated with a standard zinc curve. The determination of the zinc to protein ratio of the purified protein from the CMC column was made as follows:

The lyophilized eluates were dissolved in water. The weight of phosphate is known from the volume of solution lyophilized. The weight from the lyophilized sample the NaCl concentration was calculated. The solution was found to contain 0.19 M NaCl, 0.011 M phosphate and a small amount of protein. A standard zinc curve was then determined (by flameless atomic absorption spectrophotometry) in solutions containing these concentrations of NaCl and phosphate.

Zinc concentration in two dilutions of the purified protein were obtained by direct comparison with the standard curve. Concentration of the purified protein was determined by comparing the absorption at 210 nm and 205 nm in a Cary Model 14 spectrophotometer (obtained from Applied Physics Corp., Monrovia, Cal.) with that of a group of seven well known purified proteins. The mean optical density for a 1% solution of these standard proteins was 214 ± 14 (mean ± 1 Standard Deviation) and 328 ± 14, respectively, at 210 nm and 205 nm.

Finally, an amino acid analysis was performed on two separate preparations of the purified protein with a Beckman Model 121 automatic amino acid analyser after hydrolysis in 6 N HCl at 108° C. for 24, 48, and 72 hours in an oxygenfree nitrogen atmosphere. The Model 121 was obtained from Beckman Instruments of Fullerton, Cal.

Values for serine, threonine, and aspartic acid were corrected for losses by extrapolation to 0 time. Values obtained at 72 hours were used for leucene and proline. For the other amino acids, values were averaged for the 3 time periods. Methionine and half-cysteine were determined after performic acid oxydization by a modification of the method of Hirs. See *Methods of Enzymology* (Hirs. Ed.) 197–199 (1967).

Tryptophan concentration was estimated from the protein absorption at 280 nm and from the tyrosine content as determined from the amino acid analysis. Molar extinction coefficient values of 5500 and 1200 were used for tryptophanyl and tyrosyl absorption at 280 nm respectively. See Wetlaufer *Advan. Prot. Chem.*, 17: 303 (1962).

Table I below illustrates the specific activities and yield of parotid zinc protein. The yield is defined in the relative amount of absorption ($\Delta 215$) in the tube selected from the specific column compared to the amount of absorption ($\Delta 215$) in the original, whole parotid saliva.

The amino acid composition of the purified zinc protein is shown at Table II below.

It should be noted that the protein contains a rather large amount of histidine representing more than 8% of the residues. No carbohydrate, however, was detected in the purified zinc protein.

TABLE II
AMINO ACID COMPOSITION OF HUMAN PAROTID ZINC PROTEIN

| Amino Acid | Residues/37000 g protein* | Assumed integers |
|---|---|---|
| Lysine | 12.3 | 12 |
| Histidine | 20.3 | 20 |
| Arginine | 15.0 | 15 |
| Aspartic Acid | 37.3 | 37 |
| Threonine | 24.1 | 24 |
| Serine | 22.0 | 22 |
| Glutamic Acid | 35.2 | 35 |
| Proline | 19.0 | 19 |
| Glycine | 23.3 | 23 |
| Alanine | 17.0 | 17 |
| Valine | 23.9 | 24 |
| Half-Cysteine | 1.6 | 2 |
| Methionine | 3.7 | 4 |
| Isoleucine | 12.9 | 13 |
| Leucine | 24.0 | 24 |
| Tyrosine | 19.0 | 19 |
| Phenylalanine | 9.3 | 9 |
| Tryptophan+ | 4.9 | 5 |
| Total | | 324 |

*Corrected for losses based upon a molecular weight of 37,000
+Estimated from protein absorption at 280 nm and from the tyrosine content as determined from the amino acid analysis.

Zinc Levels in Blood and Parotid Saliva

Saliva was collected from many subjects, both men and women in whom normal taste acuity was demonstrated, and from 47 patients, 20 men and 27 women, with hypogeusia of various etiologies. Blood was also collected from the antecubital vein of these and other subjects, allowed to clot, centrifuged, and the serum removed.

Table III below records the zinc levels found in these fluids. It should be noted that the number in parentheses corresponds to the number of subjects.

TABLE III
SERUM AND PAROTID ZINC LEVELS IN NORMAL SUBJECT AND IN PATIENTS WITH HYPOGEUSIA

| Condition | Serum Zinc ppm | Parotid Zinc ppb |
|---|---|---|
| Normal Subjects | 96 ± 2* (150) | 51 ± 3 (34) |
| Patients with Hypogeusia | 77 ± 2‡ (125) | 10 ± 1‡ (47) |

+Hypogeusia of the patients was related to several etiological factors
*Mean ± SEM (Standard Error of the Mean)
‡$p<0.001$ with respect to normals Serum zinc concentrations were determined by flame aspiration atomic absorption spectrophotometry.

Both serum and parotid zinc concentrations in subjects with normal taste acuity were found to be significantly higher. The difference between the means of the two groups were evaluated according to the Student "t" test ($p<0.001$). In normal subjects the ratio of parotid zinc to serum zinc was found to be $0.5 \times 10^{-3}$ whereas in patients with hypogeusia this ratio is significantly lower, i.e., $0.1 \times 10^{-3}$ indicating that a more profound decrease in zinc occurred in saliva of these

TABLE I
SPECIFIC ACTIVITIES AND YIELD OF PAROTID ZINC PROTEIN

| Substance | Tubes | Specific Activity Zn (ppb)/$\Delta 215$ | Specific Activity Zn (ppb)/280 nm (OD) | Yield of Parotid Zinc Protein % |
|---|---|---|---|---|
| Whole parotid saliva | | 1.1 | 5.2 | |
| Sephadex G 150 Column | 35–39 | 9.4 | 470 | 5.9 |
| DEAE-A50 Column* | 14–34 | 63 | 530 | 0.4 |
| CMC Column | 190–218 | 210 | 800 | 0.06 |

*The second zinc for peak was used to avoid the overlap with the strong $\Delta 215$ peak preceding the zinc peaks.

patients than in their serum. Table III summarizes these results.

In order to further evaluate the zinc protein $^{65}$Zn was injected intraveneously into a woman subject. The $^{65}$Zn appeared in the parotid saliva within 20 minutes and the level thereof continued to increase for 6–8 hours while the blood level was rapidly falling off, before levelling off. Fractionation of this saliva on the Sephadex G 150 column revealed a $\gamma$Zn peak which coincided with that of Fraction II (See FIG. ) and the ratio of $\gamma$NZ to indogeneous, non-radioactive zinc was constant across the Fraction IIA. This same result was obtained in 15 separate studies from saliva collected from this patient over a period of four months. These results suggest the zinc is rapidly incorporated into the zinc protein in vivo.

The function of the protein in the taste process is further suggested by the lower than normal levels of salivary zinc found in patients with hypogeusia and by the demonstration of significantly lower values for Zn/$\Delta$215 in Fraction II in patients with hypogeusia as compared to normal subjects following total protein fractionation on the Sephadex G-150 column. Patients having hypogeusia exhibited a Zn/$\Delta$215 of $8 \pm 1$ compared to the normal level of $25 \pm 3$.

Accordingly, the process of this invention involves the discovery that a total protein fractionation of saliva may be achieved by subjecting whole saliva to a molecular sieve while recording three protein parameters, i.e. the presence of the peptide chromophore, absorbance at 215 nm (or more properly $\Delta$215 to correct for absorption due to turbidity); the amount of tyrosine and tryptophan, absorbance at 280 nm; and the tryptophan quantum yield, fluorescence at 340 nm. These three protein parameters are then recorded against the zinc concentration as a marker. This fractionation process may then be used as a diagnostic tool to determine abnormalities in human saliva.

As an example of use of the total fractionation process of this invention, the process was used to isolate a new zinc protein in saliva by maximizing the three protein parameters and the zinc concentration parameter. Following molecular sieve fractionation it was observed that the ratio of zinc concentration to the three parameters maximized in a range corresponding to a molecular weight of from about 60,000 to about 80,000. The aliquots corresponding to this range were then further subjected to a combined molecular sieve and ion exchange purification while the three protein parameters and the zinc concentration were once again recorded.

The aliquots maximizing the parameters in the second, combined molecular sieving and ion exchange purification where then subjected to a final purification by ion exchange which developed the purified protein having a constant zinc to protein ratio and constant ratio of each protein parameter to the others.

Subsequent evaluations indicated that the protein had a molecular weight of 37,000, and contained two moles zinc per mole of protein.

Clinical evaluation of patients suffering with hypogeusia, indicated a statistically significant lower ratio of parotid zinc to serum zinc than that of subjects having demonstrated normal taste acuity. Furthermore, patients suffering from hypogeusia also demonstrated significantly lower values for the zinc/$\Delta$215 ratio in the molecular range of Fraction II in FIG. 1, about 80,000 upon total protein fractionation of saliva.

Accordingly, by utilizing the fractionation process of this invention it was determined that patients suffering from hypogeusia suffer a marked deficiency in the newly discovered zinc protein, gustin, in saliva which deficiency is far greater than the deficiency previously noted in blood serum zinc concentration.

The invention may be embodied in other specific forms without departing from the spirit or essential characteristics thereof. The present embodiment are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A method for analyzing saliva to determine the total protein content thereof comprising the steps of:
   fractionating the protein components of said saliva on a molecular sieve, said protein components separating as a function of their molecular weights and aromaticity;
   collecting separate aliquots of said fractionated saliva;
   measuring protein parameters dependent upon (1) the amount of the peptide chromophore; (2) the amount of tyrosine and tryptophan; and (3) the quantum yield of tryptophan; and (4) the zinc concentration in each aliquot;
   recording said measured parameters to provide a total protein fractionation record.

2. The method of claim 1 wherein said fractionation is by gel filtration.

3. The method of claim 1 wherein said parameters are the absorption at 215 nm, corrected for absorption due to turbidity; absorption at 280 nm; and fluorescence at 340 nm, with excitation at 280 nm.

4. The method of claim 3 wherein absorption at 215 nm is corrected for absorption due to turbidity by measuring the difference between absorption at 225 nm and absorption at 215 nm.

5. The method of claim 1 wherein said saliva is initially collected, cooled, and treated to remove flocculent and insoluble protein before subjecting said saliva to molecular separtion.

6. The method claim claim 5 wherein said cooled saliva is treated by centrifugation at about 20,000 xg for about 30 minutes at 0° C.

7. A method for isolating and identifying a zinc protein from human saliva comprising the steps of:
   fractionating the protein components of said saliva on a molecular sieve, said protein components separating as a function of their molecular weights and aromaticity;
   collecting separate aliquots of said fractionated saliva;
   measuring protein parameters dependent upon (1) the amount of the peptide chromophore; (2) the amount of tyrosine and tryptophan; and (3) the quantum yield of tryptophan and (4) the zinc concentration in each aliquot;
   selecting those aliquots wherein the zinc concentration to protein parameters ratios are maximum;
   subjecting the selected aliquot fraction to a combined molecular sieve and ion exchange component separation;
   collecting separate aliquots of said separated material;

measuring protein parameters dependent upon (1) the amount of the peptide chromophore; (2) the amount of tyrosine and tryptophan; and (3) the quantum yield of tryptophan and (4) the zinc concentration in each aliquot;

selecting those aliquots wherein the zinc concentration to protein parameters are maximum;

subjecting the selected aliquot fraction to a final purification by ion exchange;

collecting separate aliquots of said material;

measuring the protein parameters dependent upon (1) the amount of the peptide chromophore; (2) the amount of tyrosine and tryptophan; and (3) the quantum yield of tryptophan and (4) the zinc concentration in each aliquot;

selecting those aliquots wherein the zinc concentration to protein parameter ratios are constant and the ratios of the parameters are constant to each other.

8. The method of claim 7 wherein said initial molecular sieve component fractionation is by gel filtration.

9. The method of claim 7 wherein said parameters are the absorption at 215 nm, corrected for absorption due to turbidity; absorption at 280 nm; and fluorescence at 340 nm, with excitation at 280 nm.

10. The method of claim 9 wherein absorption at 215 nm is corrected for absorption due to turbidity by measuring the difference between absorption at 225 nm and absorption at 215 nm.

11. The method of claim 7 wherein said saliva is initially collected, cooled and treated to remove flocculent and insoluble protein before subjecting said saliva to said initial molecular separation.

12. The method of claim 7 wherein the aliquots selected after said initial molecular sieve component separation comprise components having molecular weights of from about 60,000 to about 80,000.

13. The method of claim 11 wherein said cooled saliva is treated by centrifugation at about 20,000 xg for about 30 minutes at about 0° C. before subjecting said saliva to the molecular sieve component separation.

14. A method for diagnosing zinc deficiency and evaluating zinc nutriture comprising the steps of:
collecting saliva and subjecting said saliva to a total protein fractionation while measuring protein parameters dependent upon (1) the amount of the peptide chromophore; (2) the amount of tyrosine and tryptophan; and (3) the quantum yield of tryptophan; and (4) the zinc concentration;
recording said measured results for evaluation of said recorded results against normal values.

15. The method of claim 14 wherein said fractionation is by gel filtration.

16. The method of claim 14 wherein said parameters are the absorption at 215 nm, corrected for absorption due to turbidity; absorption at 280 nm, and fluorescence at 340 nm with excitation at 280 nm.

17. The method of claim 16 wherein absorption at 215 nm is corrected for absorption due to turbidity by measuring the difference between absorption at 225 nm and absorption at 215 nm.

18. The method of claim 14 wherein said saliva is initially collected, cooled, and treated to remove flocculent and insoluble protein before subjecting said saliva to total protein fractionation.

19. The method of claim 18 wherein said cooled saliva is treated by centrifugation at about 20,000 xg for about 30 minutes at 0° C.

20. The method of claim 14 wherein said saliva is initially fractionated on a molecular sieve, the protein components separating as a function of their molecular weights and aromaticity, and collected in separate aliquots, the protein parameters and zinc concentration of each aliquot being recorded for evaluation.

21. The method of claim 20 further comprising selecting those aliquots wherein the zinc concentration to protein parameters ratio are maximum;
subjecting the selected aliquot fraction to a combined molecular sieve and ion exchange component separation; collecting separate aliquots of said separated material; measuring protein parameters dependent upon (1) the amount of peptide chromophore; (2) the amount of tyrosine and tryptophan; and (3) the quantum yield of typtophan and (4) the zinc concentration in each aliquot; selecting those aliquots wherein the zinc concentration to protein parameters are maximum;
subjecting the selected aliquot fraction to a final purification by ion exchange;
collecting separate aliquots of said material; measuring the protein parameters dependent upon (1) the amount of peptide chromophore; (2) the amount of tyrosine and tryptophan; and (3) the quantum yield of tryptophan and (4) the zinc concentration in each aliquot; selecting those aliquots wherein the zinc concentration to protein parameter ratios are constant and the ratio of each protein parameter to each other is constant for evaluation.

22. A method for diagnosing diseases of protein synthesis or diseases characterized by the presence of abnormal proteins or abnormal protein synthesis comprising the steps of:
collecting saliva and subjecting said saliva to a total protein fractionation while measuring protein parameters dependent upon (1) the amount of the peptide chromophore; (2) the amount of tyrosine and tryptophan; and (3) the quantum yield of tryptophan; and (4) the zinc concentration;
recording said measured results for evaluation of said recorded results against normal values.

23. The method of claim 22 wherein said fractionation is by gel filtration.

24. The method of claim 22 wherein said parameters are the absorption at 215 nm, corrected for absorption due to turbidity; absorption at 280 nm; and fluorescence at 340 nm with exitation at 280 nm.

25. The method of claim 24 wherein absorption at 215 nm is corrected for absorption due to turbidity by measuring the difference between absorption at 225 nm and absorption at 215 nm.

26. The method of claim 22 wherein said saliva is initially collected, cooled, and treated to remove flocculent and insoluble protein before subjecting said saliva to total protein fractionation.

27. The method of claim 26 wherein said cooled saliva is treated by centrifugation at about 20,000 xg for about 30 minutes at 0° C.

28. The method of claim 22 wherein said saliva is initially fractionated on a molecular sieve, the protein components separating as a function of their molecular weights and aromaticity, and collected in separate aliquots, the protein parameters and zinc concentration of each aliquot being recorded for evaluation.

29. The method of claim 28 further comprising selecting those aliquots wherein the zinc concentration to protein parameters ratios are maximum;

subjecting the selected aliquot fraction to a combined molecular sieve and ion exchange components separation; collecting separate aliquots of said separated material; measuring protein parameters depending upon (1) the amount of peptide chromophore; (2) the amount of tyrosine and tryptophan; and (3) the quantum yield of tryptophan and (4) the zinc concentration in each aliquot; selecting those aliquots wherein the zinc concentration to protein parameters are maximum;

subjecting the selected aliquot fraction to a final purification by ion exchange;

collecting separate aliquots of said material; measuring the protein parameters dependent upon (1) the amount of peptide chromophore; (2) the amount of tyrosine and tryptophan; and (3) the quantum yield of tryptophan and (4) the zinc concentration in each aliquot; selecting those aliquots wherein the zinc concentration to protein parameter ratios are constant and the ratios of the protein parameters to each other are constant for evaluation.

30. A method for diagnosing taste dysfunction comprising the steps of:

collecting saliva and subjecting said saliva to a total protein fractionation while measuring protein parameters dependent upon (1) the amount of the peptide chromphore; (2) the amount of tyrosine and tryptophan; and (3) the quantum yield of tryptophan; and (4) the zinc concentration;

recording said measured results for evaluation of said recorded results against normal values.

31. The method of claim 30 wherein said fractionation is by gel filtration.

32. The method of claim 30 wherein said parameters are the absorption at 215 nm, corrected for absorption due to turbidity; absorption at 280 nm; and fluorescence at 340 nm with excitation at 280 nm.

33. The method of claim 32 wherein absorption at 215 nm is corrected for absorption due to turbidity by measuring the difference between absorption at 225 nm and absorption at 215 nm.

34. The method of claim 30 wherein said saliva is initially collected, cooled, and treated to remove floccuent and insoluble protein before subjecting said saliva to total protein fractionation.

35. The method of claim 34 wherein said cooled saliva is treated by centrifugation at about 20,000 xg for about 30 minutes at 0° C.

36. The method of claim 30 wherein said saliva is initially fractionated on a molecular sieve, the protein components separating as a function of their molecular weights and aromaticity, and collected in separate aliquots, the protein parameters and zinc concentration of each aliquot being recorded for evaluation.

37. The method of claim 36 further comprising selecting those aliquots wherein the zinc concentration to protein parameters ratios are maximum;

subjecting the selected aliquot fraction to a combined molecular sieve and ion exchange component separation; collecting separate aliquots of said separated material; measuring protein parameters dependent upon (1) the amount of peptide chromphore; (2) the amount of tyrosine and tryptphan; and (3) the quantum yield of tryptophan and (4) the zinc concentration in each aliquot; selecting those aliquots wherein the zinc concentration to protein parameters are maximum;

subjecting the selected aliquot fraction to a final purification by ion exchange;

collecting separate aliquots of said material; measuring the protein parameters dependent upon (1) the amount of peptide chromophore; (2) the amount of tyrosine and tryptophan; and (3) the quantum yield of tryptophan and (4) the zinc concentration in each aliquot; selecting those aliquots wherein the zinc concentration to protein parameter ratios are constant and the ratio of each protein parameter to each other is constant for evaluation.

* * * * *